United States Patent [19]

Rains et al.

[11] Patent Number: 5,476,970
[45] Date of Patent: * Dec. 19, 1995

[54] METHOD FOR PREPARING ARYL KETONES

[75] Inventors: Arlice E. Rains, Chattanooga, Tenn.; Terry E. Lea, Ringgold, Ga.; David I. Templer, Arlington Heights, Ill.

[73] Assignee: Velsicol Chemical Corporation, Chattanooga, Tenn.

[*] Notice: The portion of the term of this patent subsequent to Mar. 29, 2011, has been disclaimed.

[21] Appl. No.: 197,465

[22] Filed: Feb. 16, 1984

Related U.S. Application Data

[63] Continuation of Ser. No. 963,120, Oct. 19, 1992, abandoned, which is a continuation of Ser. No. 879,053, Apr. 30, 1992, Pat. No. 5,298,684, which is a continuation of Ser. No. 707,643, May 30, 1991, abandoned.

[51] Int. Cl.$^6$ .................................................. C07C 45/45
[52] U.S. Cl. .......................................................... 568/323
[58] Field of Search ..................................... 568/319, 323

[56] References Cited

U.S. PATENT DOCUMENTS

| | | | |
|---|---|---|---|
| 2,386,007 | 10/1945 | Schmerling et al. | 568/319 |
| 2,528,789 | 3/1959 | Sachanen et al. | 568/319 |
| 2,879,296 | 3/1959 | Prill | 568/319 |
| 2,879,297 | 3/1959 | Prill et al. | 568/319 |
| 3,833,677 | 9/1974 | Grard | 568/319 |
| 3,883,594 | 5/1975 | Schmerling | 568/319 |
| 3,907,837 | 9/1975 | Effenberger et al. | 568/319 |
| 3,933,917 | 1/1976 | Schaffner et al. | 568/319 |
| 4,025,580 | 5/1976 | Taylor | 568/319 |
| 4,251,675 | 2/1981 | Engel | 568/319 |
| 4,453,012 | 6/1984 | Desbois | 568/319 |
| 4,454,350 | 6/1984 | Desbois | 568/319 |
| 4,618,726 | 10/1986 | Desbois | 508/319 |
| 4,814,508 | 3/1989 | Gors et al. | 568/319 |
| 4,922,026 | 5/1990 | Baker et al. | 568/319 |

FOREIGN PATENT DOCUMENTS

| | | | |
|---|---|---|---|
| 7303781 | 2/1973 | France | 568/319 |
| 8217692 | 10/1982 | France | 568/319 |
| 3551570 | 7/1970 | United Kingdom | 568/319 |

OTHER PUBLICATIONS

Tsukervanik et al., (1971), Chem. Absts. 74: 313, abst. 53226n.
Pearson and Buehler, Synthesis (Oct. 1972) 533–542.
Mil'to et al., 1990, Chem. Absts. 113: 6001. Abst 23274h.

*Primary Examiner*—James H. Reamer
*Attorney, Agent, or Firm*—Banner & Allegretti, Ltd.

[57] ABSTRACT

The present invention relates to the production of aryl ketones. Specifically the invention relates to the production of aryl ketones by reaction of aromatic hydrocarbon compounds and benzoyl chloride in the presence of iron (III) chloride. In particular, the invention relates to reaction under conditions of elevated temperature and pressure. Preferred embodiments of the invention specifically relate to the synthesis of benzophenone, methylbenzophenone and dimethylbenzophenone.

28 Claims, 2 Drawing Sheets

*FIG. 1*

FIG. 2

METHOD FOR PREPARING ARYL KETONES

This application is a continuation of application Ser. No. 07/963,120, filed Oct. 19, 1992, now abandoned, which is a continuation of U.S. patent application Ser. No. 07/879,053, filed Apr. 30, 1992, U.S. Pat. No. 5,298,684 which is a continuation of U.S. patent application 07/707,643, filed May 30, 1991 abandoned.

BACKGROUND OF THE INVENTION

1. Field of the Invention

The present invention relates to the production of aryl ketones by the reaction of aromatic hydrocarbon compounds and benzoyl chloride in the presence of iron (III) chloride. In particular, the invention relates to reaction under conditions of elevated temperature and pressure. The invention specifically relates to the synthesis of benzophenone, methylbenzophenone and dimethylbenzophenone.

2. Information Disclosure Statement

Aryl ketones such as benzophenone are important organic reagents used as fixatives for heavy perfumes and soaps and are used in the manufacture of a variety of pharmaceuticals, industrial chemicals and insecticides.

The usual method of synthesis of aryl ketones involves the reaction of an aromatic hydrocarbon or halogenated aromatic hydrocarbon with an aromatic or aliphatic acyl halide in the presence of stoichiometric amounts of $AlCl_3$. The product of this reaction is an aluminum chloride derivative of the aryl ketone that must be hydrolyzed to provide the final ketone product. This reaction scheme has a number of inherent economic and practical disadvantages, including the need for the final hydrolysis step; the consumption in the reaction of stoichiometric amounts of $AlCl_3$; the production of a large amount of aluminum chloride residue from the reaction that must be recycled or discarded; and the production of large quantities of waste water contaminated with the aromatic hydrocarbon that must be treated and detoxified before disposal. The development of alternative methods of synthesis is desirable.

The use of iron (III) chloride as a catalyst for the synthesis of aryl ketones has been described in the prior art.

Prill. U.S. Pat. No. 2,879,296 teaches the use of ferric chloride as a catalyst for the production of halogenated aromatic keyones from mixtures of halogenated aromatic hydrocarbons such as chlorobenzene and an acylating agent such as benzoyl chloride.

Prill and Kosmin, U.S. Pat. No. 2,879,297 teach the synthesis of diaryl ketones from aromatic carboxylic acid, aromatic compounds capable of acylation and aryltrichloromethane, the reaction catalyzed by Friedel-Crafts cataysts such as iron (III) chloride and $AlCl_3$, as well as other cataysts such as metallic zinc. Grard, U.S. Pat. No. 3,833,677 teaches the production of substituted and unsubstituted aromatic ketones from benzoyl halides and substituted or unsubstituted aromatic compounds such as benzene, catalyzed by metallic halides of the class consisting of ruthenium, osmium, rubidium and coordination complexes of such substances at temperatures from 50°–300° C.

Effenberger et al., U.S. Pat. No. 3,907,837 teach the preparation of aromatic ketones by reaction of aromatic compounds with acyl chlorides or acyl anhydrides in the presence of catalytic amounts of aromatic polynitrosulfonic acid. These inventors describe the synthesis of benzophenone from mixtures of benzene and benzoyl chloride at 160° C. and superatmospheric pressure using trinitrobenzenesulfonic acid as a catalyst.

Schaffner et al., U.S. Pat. No. 3,933,917 relates to the production of anthraquinone-1-carboxylic acid via a reaction pathway that features dimethylbenzophenone as an intermediate.

Taylor, U.S. Pat. No. 4,025,580 teaches the modification of styrene and polystyrene and derivatives by acylation using aromatic acid chlorides such as benzoyl chloride and catalysts such as iron (III) chloride.

Gors et al., U.S. Pat. No. 4,814,508 relates to the production of aromatic ketones using a mixture of a Lewis acid such as iron (III) chloride and a Lewis base such as an organic amide in an aprotic solvent such as methylene chloride.

The use of elevated temperature and/or pressure for the synthesis of aryl ketones has been described in the prior art.

Schmerling and Ipatieff, U.S. Pat. No. 2,386,007 relates to the production of alkyl and aryl ketones from aromatic hydrocarbons and alkyl or aryl acid chlorides using $ZnCl_2$ as a catalyst. The synthetic reaction proceeds at pressures of up to 200 atmospheres (atms) and temperatures of 100°–350° C.

Sachanen and Caesar, U.S. Pat. No. 2,528,789 teach the synthesis of benzophenone from benzene and benzoyl chloride using temperatures of 300°–700° C. and pressures of 1750–2500 $lb/in^2$ (psi; 119–170 atms) in the absence of a catalyst.

Schmerling, U.S. Pat. No. 3,883,594 relates to the production of aromatic ketones and alkylated derivatives thereof by reaction between an aromatic hydrocarbon and an acyl halide in the presence of a Friedel-Crafts catalyst and a saturated hydrocarbon containing at least one tertiary carbon atom.

Desbois, U.S. Pat. No. 4,453,012 relates to the synthesis of phenylketones from halo- or trihalomethylbenzenes in the presence of hydrofluoric acid and boron trifluoride under a pressure exceeding 1 atm.

Desbols, U.S. Pat. No. 4,454,350 relates to the acylation of halo- or trihalomethylbenzene by reaction with a carboxylic acid in the presence of hydrofluoric acid and boron trifluoride under a pressure exceeding 1 atm.

Desbois, U.S. Pat. No. 4,618,726 relates to the synthesis of benzophenone from derivatives of benzene substituted with deactivating groups and phosgene in the presence of hydrofluoric acid and boron trifluoride.

Baker et al., U.S. Pat. No. 4,922,026 provides for the acylation of benzene, toluene or anisole using difunctional acyl halides or anhydrides of organic acids and catalytic amounts of iron (III) chloride at temperatures of 50°–300° C. and pressures of 10–1000 psi (0.7–70 atm). The preferred acylating agent is isophthaloyl chloride.

Engel, U.S. Pat. No. 4,251,675 teaches the synthesis of diphenylmethane from benzene and benzyl chloride in the presence of $FeCl_2$ catalyst.

Pearson and Buehler, Synthesis (Oct. 1972) 533–542 disclose Friedel-Crafts acylation using little or no catalyst in a reaction performed at elevated temperatures and atmospheric pressure.

The prior art thus contains numerous attempts to develop efficient and economically advantageous methods of aryl ketone synthesis. The present invention relates to the use of iron (III) chloride in catalytic amounts for the production of aryl ketones from aromatic hydrocarbon compounds and benzoyl chloride under conditions of elevated temperature and pressure. The teachings of the present invention describe a novel and unexpected combination of temperature, pressure and an amount of iron (III) chloride that efficiently and economically produces high yields of aryl ketones. While the related art teaches the synthesis of benzophenone from benzene and benzoyl chloride, the use of iron (III) chloride in the synthesis of benzophenone, and the use of conditions of elevated temperature and pressure for benzophenone synthesis, it neither teaches nor suggests the combination of the use of catalytic amounts of $FeCl_3$ under conditions of elevated temperature and pressure for the synthesis of benzophenone as described in the present invention.

BRIEF SUMMARY OF THE INVENTION

The present invention relates to the production of aryl ketones. More specifically the invention relates to methods for the synthesis of aryl ketones from aromatic hydrocarbon compounds and benzoyl chloride. In particular, the invention provides for the synthesis of aryl ketones in the presence of iron (III) chloride and under conditions of elevated temperature and pressure.

An object of the invention is to provide efficient methods for the synthesis of an aryl ketone. An advantage of the present invention is the production of a substantially pure aryl ketone in a single reactive step. In preferred embodiments, the aryl ketone is benzophenone, methylbenzophenone and dimethylbenzophenone.

It is an object of the present invention to provide methods for the synthesis of an aryl ketone from aromatic hydrocarbon compounds. In preferred embodiments, the aromatic hydrocarbon is selected from the group comprising benzene, toluene and xylenes.

It is an additional object of the present invention to provide a method for the synthesis of an aryl ketone using benzoyl chloride.

It is another object of the invention to provide methods for the synthesis of an aryl ketone utilizing reaction mixtures comprising a ratio of the aromatic hydrocarbon equal to or in excess of the benzoyl chloride in the presence of a catalytic amount of iron (III) chloride.

An object of the present invention is to provide methods for the synthesis of an aryl ketone in the presence of iron (III) chloride. It is a particular object of the present invention to provide economical methods for the synthesis of an aryl ketone in the presence of catalytic amounts of iron (III) chloride. The use of an inexpensive inorganic catalyst is an advantage of the present invention. An additonal advantage of the present invention is the use of catalytic rather than stoichiometric amounts of iron (III) chloride. It is an additional advantage of the present invention that the production of aryl ketone is accomplished without the concomitant production of a large amount of residual inorganic waste material.

Another advantage of the present invention is that the use of catalytic amounts of iron (III) chloride as provided by the invention does not involve the production of toxic or hazardous residual waste. The small amount of organic and inorganic residue produced according to the teachings of the present invention can be easily and routinely discarded without the need for extensive or expensive handling or treatment.

It is an object of the present invention to provide a method for the synthesis of an aryl ketone under conditions of elevated temperature.

It is a further object of the present invention to provide methods for the synthesis of an aryl ketone under conditions of greater than atmospheric pressure.

It is a particular object of the present invention to provide a method for the synthesis of an aryl ketone under conditions of elevated temperature and pressure greater than atmospheric and sufficient to maintain the aromatic hydrocarbon substantially in a liquid form.

It is an object of the present invention to provide an efficient method for the synthesis of an aryl ketone comprising the step of incubating a reaction mixture under conditions of temperature and pressure sufficient to maintain the aromatic hydrocarbon substantially in a liquid form and for a time sufficient to substantially convert the benzoyl chloride to the aryl ketone and hydrochloric acid gas. It is an advantage of the present invention that this reaction results in substantial conversion of the benzoyl chloride to aryl ketone and hydrochloric acid gas. It is an additional advantage of the invention that the conditions provided by the invention result in the substantial conversion of the benzoyl chloride to ketone and hydrochloric acid gas without requiring the reaction to proceed for an uneconomically long time.

It is an additional object of the present invention to provide a method for the synthesis of an aryl ketone wherein the benzoyl chloride provided in the reaction mixture provided by the invention is substantially converted to the aryl ketone and hydrochloric acid gas.

It is a particular object of the invention to provide a method for the synthesis of aryl ketones under conditions of elevated temperature and pressure greater than atmospheric whereby the hydrochloric acid gas produced in the reaction is vented from the reaction vessel whilst the superatmospheric pressure of the reaction is maintained.

It is also an object of the present invention to provide a method for the synthesis of an aryl ketone that is substantially a pure aryl ketone.

It is also an object of the present invention to provide a method for the synthesis of a substantially pure aryl ketone in an economically efficient time.

In a first aspect, the present invention provides a method for the synthesis of an aryl ketone comprising the step of incubating a reaction mixture comprising an aromatic hydrocarbon and benzoyl chloride in the presence of a catalytic amount of iron (III) chloride at a temperature and for a time sufficient to substantially convert benzoyl chloride to the aryl ketone and hydrochloric acid gas under a pressure greater than atmospheric and sufficient to maintain the aromatic hydrocarbon substantially in a liquid form. Preferred pressures range fromm 100–450 pounds per square inch. The reaction vessel is preferably vented so as to allow the release of the hydrochloric acid gas whilst maintaining the reaction under greater than atmospheric pressures. In preferred embodiments the aryl ketone is benzophenone, methylbenzophenone or dimethylbenzophenone.

In another aspect, the invention provides a method for preparing an aryl ketone comprising the following steps in the following sequence:

(a) heating a reaction mixture comprising an aromatic hydrocarbon, benzoyl chloride and a catalytic amount of iron (III) chloride to a temperature and for a time sufficient to substantially convert the acyl halide to the aryl ketone under a pressure greater than atmospheric and sufficient to maintain the aromatic hydrocarbon substantially in a liquid form, the pressure being from about 100 pounds per square inch to about 450 pounds per square inch, wherein the pressure is maintained in a reaction vessel that is vented to permit the release of the hydrochloric acid gas;

(b) distilling the reaction mixture to form a distillate comprising the aryl ketone product;

(c) washing the distillate with a solution of sodium hydroxide;

(d) washing the distillate with water;

(e) redistilling the washed distillate to form the substantially pure aryl ketone.

An advantage of the present invention is that the unreacted aromatic hydrocarbon is separated from the reaction mixture by distillation before the sodium hydroxide and water washes are performed. The advantage of this method is that it avoids the production of large quantities of waste water contaminated with an amount of the aromatic hydrocarbon that must be treated and detoxified before disposal as required using other synthetic processes known in the prior art.

In a further aspect, the invention provides a method for preparing an aryl ketone comprising the following steps:

(a) heating a first reaction mixture comprising an aromatic hydrocarbon and a catalytic amount of iron (III) chloride to a temperature and under a pressure greater than atmospheric and sufficient to maintain the aromatic hydrocarbon substantially in a liquid form, the pressure being from about 100 pounds per square inch to about 450 pounds per square inch;

(b) mixing the first reaction mixture with a second reaction mixture comprising benzoyl chloride to form a third reaction mixture;

(c) incubating the third reaction mixture at a temperature and for a time sufficient to substantially convert the acyl halide to the aryl ketone and hydrochloric acid gas, under a pressure greater than atmospheric and sufficient to maintain the aromatic hydrocarbon substantially in a liquid form, the pressure being from about 100 pounds per square inch to about 450 pounds per square inch; and (d) venting the reaction vessel to permit the release of an amount of the hydrochloric acid gas sufficient to maintain the pressure in the reaction vessel between about 100 pounds per square inch to about 450 pounds per square inch.

In another aspect, the present invention provides a method for preparing an aryl ketone comprising the following steps in the following sequence:

(a) heating a first reaction mixture comprising an aromatic hydrocarbon and a catalytic amount of iron (III) chloride to a temperature and under a pressure greater than atmospheric and sufficient to maintain the aromatic hydrocarbon substantially in a liquid form, the pressure being from about 100 pounds per square inch to about 450 pounds per square inch;

(b) mixing the first reaction mixture with a second reaction mixture comprising benzoyl chloride to form a third reaction mixture;

(c) incubating the third reaction mixture at a temperature and for a time sufficient to substantially convert the acyl halide to the aryl ketone under a pressure greater than atmospheric and sufficient to maintain the aromatic hydrocarbon substantially in a liquid form, the pressure being from about 100 pounds per square inch to about 450 pounds per square inch, wherein the pressure is maintained in a reaction vessel that is vented to permit the release of the hydrochloric acid gas;

(d) distilling the reaction mixture to form a distillate comprising the aryl ketone product;

(e) washing the distillate with a solution of sodium hydroxide;

(f) washing the distillate with water;

(g) redistilling the washed distillate to form the substantially pure aryl ketone.

The invention also provides a method for performing a chemical reaction to form a chemical reaction product from at least one chemical reactant, wherein the chemical reaction produces in addition at least one species of gaseous reaction product, comprising the steps of:

(a) heating in a reaction vessel a reaction mixture comprising at least one chemical reactant at superatmospheric pressure, to a temperature and for a time sufficient to form an amount of the chemical reaction product and at least one species of gaseous reaction product; and (b) venting the reaction vessel to permit the release of an amount of the gaseous reaction product sufficient to maintain the superatmospheric in the reaction vessel.

Specific preferred embodiments of the present invention will become evident from the following more detailed description of certain preferred embodiments and the claims.

DETAILED DESCRIPTION OF THE PREFERRED EMBODIMENTS

The present invention relates to the production of aryl ketones from aromatic hydrocarbon compounds and benzoyl chloride in the presence of iron (III) chloride and under conditions of elevated temperature and pressure.

The invention relates to a chemical reaction of the formula:

$$ArH + \phi COCl \xrightarrow{catalyst} ArCO\phi + HCl$$

wherein ArH is an aromatic hydrocarbon, $\phi COCl$ is benzoyl chloride, $ArCO\phi$ is an aryl ketone and HCl is hydrochloric acid gas.

The present invention provides methods for the synthesis of an aryl ketone from aromatic hydrocarbon compounds. Such aromatic hydrocarbon compounds include any substituted or unsubstituted aromatic compounds susceptible to acylation by the methods provided by the invention. In a preferred embodiment, these aromatic hydrocarbon compounds are selected from the group consisting of benzene, toluene and xylenes. The most preferred aromatic hydrocarbon compound is benzene.

The invention also provides methods for the synthesis of an aryl ketone from benzoyl chloride, including substituted derivatives thereof.

The methods of the present invention employ reaction mixtures of the aromatic hydrocarbon and benzoyl chloride provided in a mole ratio of the reagents. Preferred mole ratios are ratios from 1:1 to about 5:1 in which the aromatic hydrocarbon is the reagent in excess. More preferred ratios are from about 3:1 to about 5:1, with the aromatic hydrocarbon in excess. The most preferred ratio is about a 4:1 excess of the aromatic hydrocarbon.

The present invention provides methods for the synthesis of an aryl ketone using iron (III) chloride.

The present invention also provides for the synthesis of an aryl ketone using catalytic amounts of iron (III) chloride. Preferred amounts of iron (III) chloride are from about 0.25% to about 3.0% of the mass of benzoyl chloride used in the reaction mixture. The most preferred amount of iron (III) chloride is from about 0.5% to about 1.0% of the mass of benzoyl chloride used in the reaction mixture.

The methods of the invention provide for the synthesis of an aryl ketone under conditions of elevated temperature and pressure greater than atmospheric. The temperature and pressure of the reaction are related to each other by their effect on the physical state of matter of the aromatic hydrocarbon compounds used in the synthesis.

Figure 1:
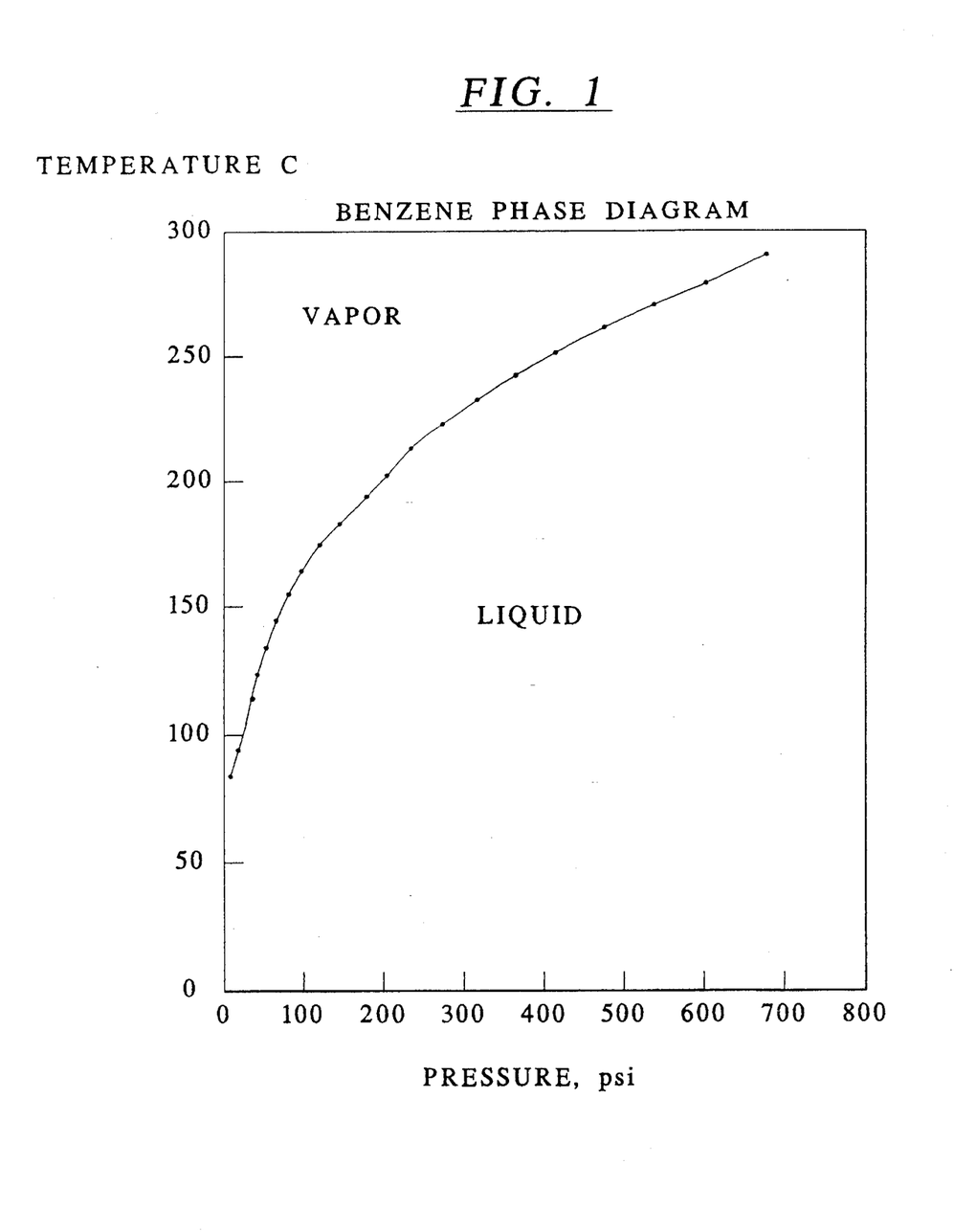
FIG. 1 is a phase diagram for benzene.

For example, FIG. 1 is a phase diagram for benzene. The diagram illustrates the physical state of benzene as either a liquid or a gas under varying conditions of temperature and pressure. The synthesis of an aryl ketone under the conditions provided by the present invention is dependent upon the existence of the aromatic hydrocarbon remaining in the liquid state of matter. As can be seen from FIG. 1, synthesis at a given temperature requires that the reaction proceed at a pressure sufficient to maintain benzene in a liquid form.

Thus, the methods of the present invention provide for the synthesis of an aryl ketone under conditions of elevated temperature. Preferred temperatures for synthesis are from about 150° C. to about 300° C. More preferred temperatures are from about 160° C to about 250° C. The most preferred temperatures are from about 170° C. to about 210° C.

The methods of the present invention also provide for the synthesis of an aryl ketone under conditions of pressure greater than atmospheric. The preferred pressures are from about 100 lb/in$^2$ (psi) to about 450 psi. More preferred pressures are from about 100 psi to about 300 psi. The most preferred pressures are from about 150 psi to about 190 psi.

The methods of the present invention provide for the synthesis of an aryl ketone under conditions of elevated temperature and pressure greater than atmospheric. The most preferred pressures are selected so that the aromatic hydrocarbon compound present in the reation mixture remains in a liquid form under the temperature conditions of the reaction.

The invention provides methods for the synthesis of an aryl ketone under conditions of elevated temperature and pressure greater than atmospheric whereby the hydrochloric acid that is generated concomitantly with the aryl ketone product is vented from the reaction vessel whilst the elevated pressure of the reaction are maintained. It is an advantage of the present invention that the hydrochloric acid side-product of the reaction is so vented, as this removes one of the back-reactants from the reaction and thereby shifts the chemical equilibrium towards more complete conversion of benzoyl chloride to aryl ketone.

The methods of the present invention provide for the synthesis of an aryl ketone under conditions of elevated temperature and pressure greater than atmospheric. The combination of temperature and pressure provided by the invention are selected so that the benzoyl chloride provided by the invention is substantially converted to aryl ketone and hydrochloric acid gas.

Preferred combinations provided by the present invention result in the production of aryl ketone that is from about 70% to about 90% of the mole quantity of benzoyl chloride provided in the reaction mixture.

The methods of the present invention provide for the synthesis of an aryl ketone under conditions of elevated temperature and pressure greater than atmospheric. The combination of temperature and pressure provided by the invention are selected so that the benzoyl chloride provided by the invention is substantially converted to aryl ketone and hydrochloric acid gas in an economically efficient reaction time. Preferred reaction times last from about 2 hours to about 15 hours. More preferred reaction times last from about 4 hours to about 10 hours. The most preferred reaction time is about 8 hours.

The methods of the present invention provide for the separation of unreacted aromatic hydrocarbon compounds from the aryl ketone. Amounts of such unreacted aromatic hydrocarbon compounds can be recycled for use in further rounds of aryl ketone synthesis. Proportions of the amounts of recycled aromatic hydrocarbon to the amount of unrecycled aromatic hydrocarbon range from about 0% to about 80%. The amount of recycled aromatic hydrocarbon will be about 65% in a reaction mixture in which the ratio of aromatic hydrocarbon to benzoyl chloride is 4:1.

Details of the embodiments of the present invention are more fully described in the following examples.

EXAMPLE 1

Preparation of Benzophenone

In the presence of catalytic amounts of iron (III) chloride, and under the appropriate conditions of temperature and pressure, benzoyl chloride and benzene react to form benzophenone and hydrochloric acid.

Figure 2:
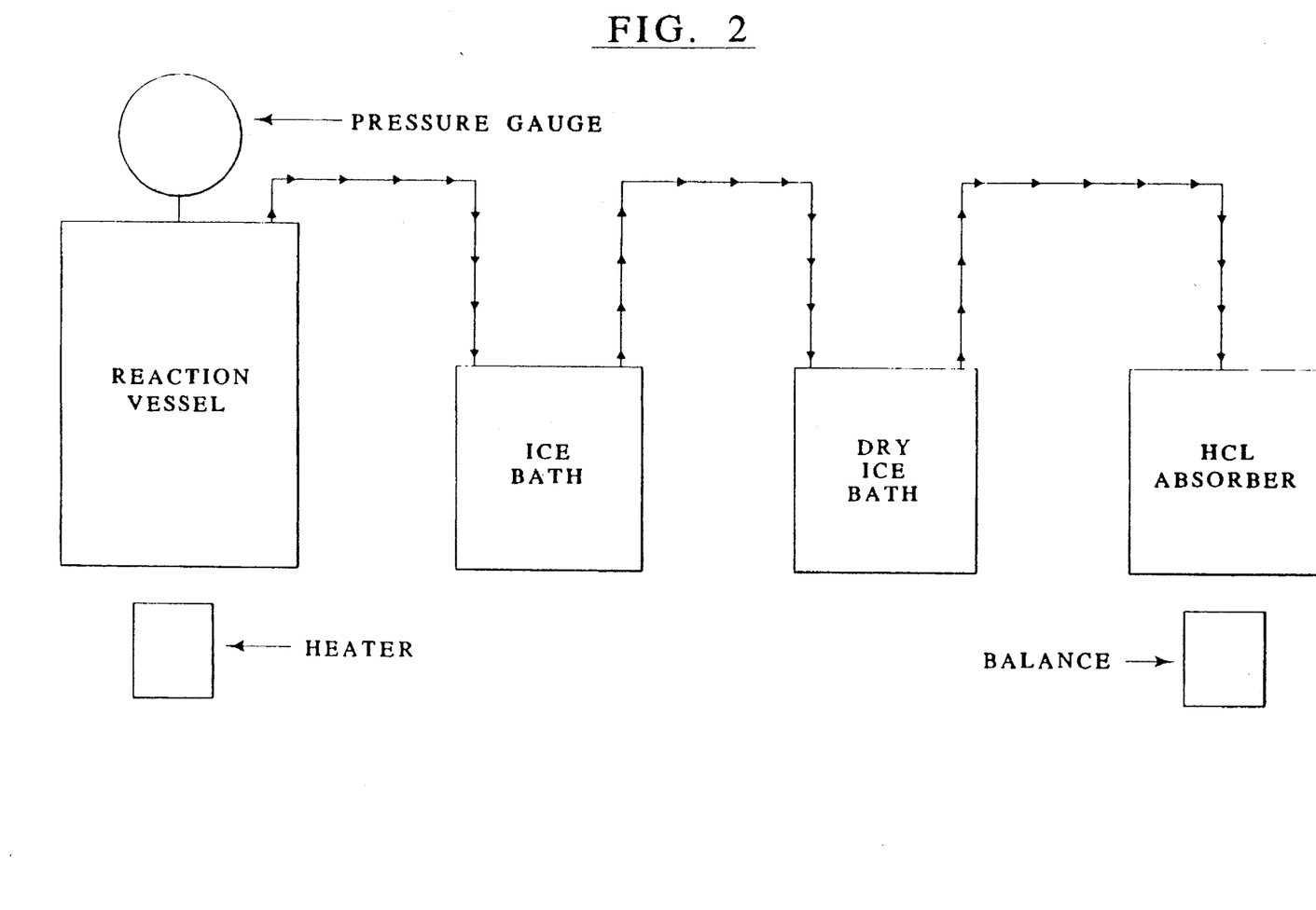
FIG. 2 illustrates the apparatus used for the reaction.

The reaction is performed using the experimental apparatus shown in FIG. 2. Benzene is typically present in the reaction mixture at a molar ratio of 4:1 in excess of benzoyl chloride. For example, 6.0 moles of benzene are mixed with 1.5 moles of benzoyl chloride and 0.013 mole (equivalent to 1.0 percent of the amount of benzoyl chloride by weight) of iron (III) chloride in a 1 liter Parr reactor. The reactor head on the reactor is secured and the assembled reactor is placed in the heater assembly. The overarm drive to the magnetic driven agitator is connected and agitation started at 50–150 revolutions per minute (rpm). At the start of the reaction all valves are closed. The hydrochloric acid gas line from the gas release valve on the reactor is connected to an ice bath, a dry ice—isopropanol bath and an ice-cold sodium hydroxide absorber (100 grams sodium hydroxide in 3500 grams of water), in that order.

The reaction mixture is then heated for about 20 minutes until a temperature of 160° C. is achieved. As the temperature increases, the pressure on the reactor increases to 175–200 pounds per square inch (psi). The gas exit valve on the reactor head is then opened and hydrochloric acid gas allowed to escape at about 60 bubbles/minute through the sodium hydroxide absorber. The pressure is maintained at 190±20 psi. The temperature is then further increased to 190° C. and the reaction allowed to proceed.

The reaction is monitored by periodically recording the increase in the weight of the sodium hydroxide absorber. The extent of the reaction is calculated from the weight increase of the absorber due to the amount of hydrochloric acid produced by the reaction, which is approximately equivalent to the amount of benzoyl chloride in the reaction that has been converted to benzophenone. The results of these calculations can be plotted as the percentage of unreacted benzoyl chloride versus time on semi-log graph paper.

The pressure on the reaction is kept at 180–190 psi by regulating the flow rate of hydrochloric acid gas release through the reactor gas release valve. Since the reaction proceeds logarithmically, an amount of hydrochloric acid equivalent to about 50% of the theoretical maximum is released in the first 2–3 hours after the reaction temperature reaches 160° C.

The reaction is allowed to proceed until the amount of hydrochloric acid produced indicates that the reaction is at least 90% complete. The reaction mass is cooled to room temperature and the reactor head removed. The reaction mass is sampled for further analysis and then transferred to the distillation apparatus.

After the reaction has gone to completion, as monitored by the amount of HCl produced, the benzophenone product is purified from the reaction mass.

The excess benzene in the reaction mixture is removed by distillation at atmospheric pressure and condensed for recycling in subsequent reaction runs. The reaction mixture is transferred to a one liter distillation flask along with the condensed benzene in the ice and dry ice traps and the benzene distilled at atmospheric pressure, to a head temperature of about 90° C. and a pot temperature of about 175° C.

Benzoyl chloride is then distilled at 100 mm Hg absolute, to a head temperature of about 140° C. and a pot temperature of about 180° C. The benzoyl chloride and benzene fractions are normally combined for recycle. As benzoyl chloride is the limiting reagent in the reaction mixture, the residual benzoyl chloride content of the reaction mixture will be low.

The benzophenone fraction of the reaction mixture is then distilled from the catalytic residue by lowering the pressure to 5–10 mm Hg Absolute, and distilling to a head temperature of about 160° C. and a pot temperature of about 225° C. The benzophenone product is recovered as a clear liquid. A crude product yield of the reaction is determined by weighing the benzophenone fraction and compensating for sampling during and after the reaction. The residual benzoyl chloride content of the benzophenone product will be about 0.3%. The distillation residue will contain the catalyst, polymers, tars and other trace components and is routinely discarded. The amount of this residue produced in a typical reaction is 0.1–0.2 lb/lb benzophenone product.

The benzophenone fraction is contaminated with a small amount (0.05–0.1 lb/lb benzophenone) of benzoic acid that co-distills with it. The benzoic acid is removed from the final product using a sodium hydroxide wash followed by 2–3 water washes. The crude benzophenone fraction is transferred to a two liter flask. To this is added 130 mls of 13% sodium hydroxide, and the mixture is heated at 70° C. for 30 minutes with agitation sufficient for good mixing. The mixture is then transferred to a separatory funnel and the organic and aqueous phases are allowed to separate. The bottom aqueous sodium hydroxide phase is decanted and discarded. The top oil phase is added back to the two liter flask.

200 mls of water are added to the oil layer in the flask and heated at 70° C. for 10 minutes while stirring with agitation sufficient for good mixing. The mixture is again transferred to the separatory funnel and the bottom oil layer of benzophenone is drained back into the two liter flask. The aqueous layer is discarded.

The water wash is repeated once or twice and the benzophenone dried by applying a vacuum of 25 mm Hg Absolute and heating to a temperature of 120° C. This drying step may be omitted if a yield determination at this step is not desired.

This procedure also removes residual benzoyl chloride. The washing procedure is performed after the residual benzene has been removed from the reaction mixture in the first distillation, since washing before this distillation would result in the production of a large amount of benzene-contaminated water and present unneccessary disposal problems.

The washed benzophenone product is given a final distillation in a 10 trays Oldershaw column to improve product color and purity. The benzophenone is distilled at 100 mm Hg Absolute and a head temperature of about 230° C. If a lower distillation temperature is desirable, the head temperature can be reduced to about 205° C. by distilling at 50 mm Hg Absolute. A small forerun fraction (about 1–3%) is removed at a 3/1 or 5/1 reflux ratio and then the main fraction is removed at a 1/1 reflux ratio. Reflux is increased to 5/1 near the end of the distillation. A small pot residue of 1.5–2.5% is obtained which is discarded. This final distillation increases the purity of the benzophenone product from about 99.5 % to about 99.9%.

EXAMPLE 2

The Effect of Temperature and Pressure on Benzophenone Production

The effect of reaction temperature and pressure on benzophenone production was determined. Reactions were performed essentially as described in Example 1. The results of representative experiments are shown in Table I:

TABLE I

| Amount of Catalyst | Temperature °C. | Pressure psi | Yield % |
|---|---|---|---|
| 3.0 % | 180 | 200 | 75.4 |
| 3.0% | 180 | 250 | 72.2 |
| 3.0% | 200 | 450 | 74.1 |
| 3.0% | 225 | 550 | 70.6 |
| 3.0% | 250 | 800 | 67.2 |
| 1.0% | 190 | 180 | 76.2 |
| 1.0% | 190 | 180 | 76.4 |
| 1.0% | 190 | 200 | 79.0 |
| 1.0% | 190 | 200 | 79.8 |
| 1.0% | 400 | 200 | 71.2 |
| 1.0% | 400 | 210 | 70.8 |
| 1.0% | 450 | 210 | 70.6 |
| 0.5% | 160–240 | 100 | 77.8 |
| 0.5% | 200–225 | 200 | 79.8 |
| 0.5% | 200 | 200 | 75.5 |
| 0.5% | 300–320 | 200 | 71.0 |
| 0.5% | 200–225 | 400 | 71.3 |
| 0.35% | 190–220 | 190 | 76.9 |
| 0.35% | 200 | 280 | 76.0 |
| 0.35% | 200 | 450 | 68.8 |

The data in Table I illustrate the effect of reaction pressure and temperature on the yield of benzophenone product. The product yield is expressed as percentage of the theoretical benzophenone yield produced from the initial benzoyl chloride charge in the reaction that is converted to product. The temperatures used at each pressure were temperatures at which benzene remained in the liquid state at that pressure. Pressures were varied between 150–550 psi; in one experiment a pressure of 800 psi was used, with a noticably detrimental effect on reaction yield. The reactions were performed for varying times until they had gone essentially to completion, as monitored by the amount of hydrochloric acid gas produced (see Example 1).

As shown in Table I, increased pressures above about 200 psi usually resulted in a decrease in the yield of benzophenone product. From these experiments it was determined that the most preferred pressure was from about 150 psi to about 190 psi. The most preferred temperature was found to be from about 170° C. to about 210° C. Under these conditions of temperature and pressure, benzene remains essentially in the liquid state of matter during the reaction. In addition, under these conditions the reaction proceeds essentially to completion in about 8 hours.

EXAMPLE 3

The Effect of the Amount of Catalyst and the Ratio of Benzene to Benzoyl Chloride on Benzophenone Production The effect of the amount of iron (III) chloride catalyst used and the ratio of benzene to benzoyl chloride in the reaction on benzophenone production was determined. Reactions were performed essentially as described in Example 1 and the amount of the iron (III) chloride catalyst used and the ratios of benzene to benzoyl chloride in the reaction were varied.

The results of representative experiments are shown in Table II:

TABLE II

| No. of Expts. | Ratio of Reagents | Amount of Catalyst | Yield | % Purity[a] |
| --- | --- | --- | --- | --- |
| 2 | 2:1 | 2.8 | 72.3 ± 2.6 | N.D. |
| 4 | 3:1 | <0.5% | 74.3 ± 3.6 | 94.6 |
| 8 | 3:1 | 0.5% | 73.1 ± 4.2 | 92.3 |
| 10 | 3:1 | 1.0% | 74.4 ± 4.9 | 92.8 |
| 6 | 3:1 | 3.0% | 77.0 ± 2.0 | 92.5 |
| 38 | 4:1 | 1.0% | 78.1 ± 4.8 | 93.8 |
| 1 | 4:1 | 3.0% | 75.3 ± N.D. | 92.2 |
| 1 | 5:1 | 1.0% | 83.2 ± N.D. | 94.4 | a = percent purity after the first distillation step
N.D. = not determined

As can be seen from this Table, the highest yields at each ratio of benzene to benzoyl chloride were obtained using no more than 1.0% of iron (III) chloride catalyst. From these experiments, the preferred amount of iron (III) catalyst was determined to be from about 0.5% to about 1.0% of the weight of the benzoyl chloride charge. A major advantage of using smaller amounts of catalyst is an improvement in the handling characteristics of the distillation residue. When 3.0% iron (III) chloride is used, the distillation residue was very viscous even at temperatures of 175° C.–200° C. However, using 1.0% iron (III) chloride resulted in a distillation residue having a pour point of between about 110° C. and about 125° C.

The effect of the relative amounts of benzene and benzoyl chloride used in the reaction on benzophenone production was determined. Reactions were performed essentially as described in Example 1 and the mole ratio of benzene to benzoyl chloride was varied between 1:1 and 5:1, benzene in excess. The results of representative experiments are shown in Table II.

The yield of benzophenone is represented as the mole percentage of the initial benzoyl chloride charge that is converted to product. As shown in Table II, the yield of benzophenone increases with the increasing ratio of benzene to benzoyl chloride. From these experiments it was determined that the preferred ratio of benzene to benzoyl chloride was from about 3:1 to about 5:1.

EXAMPLE 4

Preparation of Methylbenzophenone

Methylbenzophenone was prepared from mixtures of toluene and benzoyl chloride using essentially the method described in Example 1, with the following modifications in the distillation scheme.

The excess toluene in the reaction mixture is removed by distillation at atmospheric pressure and condensed for recycling in subsequent reaction runs. The reaction mixture is transferred to a one liter distillation flask along with condensed toluene in the ice and dry ice traps and the toluene distilled at atmospheric pressure, to a head temperature of about 115° C. and a pot temperature of about 185° C.

Benzoyl chloride is then distilled at 100 mm Hg absolute, to a head temperature of about 140° C. and a pot temperature of about 180° C. The benzoyl chloride and toluene fractions are normally combined for recycle. As benzoyl chloride is the limiting reagent in the reaction mixture, the residual benzoyl chloride content of the reaction mixture will be low.

The methylbenzophenone fraction of the reaction mixture is then distilled from the catalytic residue by lowering the pressure to 5–10 mm Hg Absolute, and distilling to a head temperature of about 160° C. and pot temperature of about 225° C. The methylbenzophenone product is recovered as a clear liquid. The crude product yield of the reaction is determined by weighing the methylbenzophenone fraction and compensating for sampling during and after the reaction. The residual benzoyl chloride content of the methylbenzophenone product will be about 0.3%. The distillation residue will contain the catalyst, polymers, tars and other trace components and is discarded. The amount of this residue produced in a typical reaction is 0.1–0.2 lb/lb methylbenzophenone product.

The methylbenzophenone fraction is contaminated with a small amount (0.05–0.1 lb/lb methylbenzophenones) of benzoic acid that co-distills with it. The benzoic acid is removed from the final product as described in Example 1. The washed methylbenzophenone product may or may not be given a final distillation in a 10 trays Oldershaw column to improve product color and purity as described in Example 1. The product consists of three geometric isomers of methylbenzophenone (ortho-, meta-, and para-). A final distillation is necessary for separation and isolation of the respective monomers.

EXAMPLE 5

Preparation of Dimethylbenzophenone

The method described in Example 1 was used to prepare dimethylbenzophenone from mixtures of o-, m- and p-xylene and benzoyl chloride.

The excess xylene in the reaction mixture is removed by distillation at atmospheric pressure and condensed for recycling in subsequent reaction runs. The reaction mixture is transferred to a one liter distillation flask along with condensed xylene in the ice and dry ice traps and the xylene distilled at atmospheric pressure, to a head temperature of about 140° C. and a pot temperature of about 200° C.

Benzoyl chloride is then distilled at 100 mm Hg absolute, to a head temperature of about 140° C. and a pot temperature of about 180° C. The benzoyl chloride and xylene fractions are normally combined for recycle. As benzoyl chloride is the limiting reagent in the reaction mixture, the residual benzoyl chloride content of the reaction mixture will be low.

The dimethylbenzophenone fraction of the reaction mixture is then distilled from the catalytic residue by lowering the pressure to 5–10 mm Hg Absolute, and distilling to a pot temperature of about 250° C. The dimethylbenzophenone product is recovered as a clear liquid. The amount of this residue produced in a typical reaction is 0.1–0.2 lb/lb dimethylbenzophenone product.

The dimethylbenzophenone fraction is contaminated with a small amount (0.05–0.1 lb/lb dimethylbenzophenones) of benzoic acid that co-distills with it. The benzoic acid is removed from the final product as described in Example 1. The washed dimethylbenzophenone product may or may not be given a final distillation in a 10 trays Oldershaw column to improve product color and purity as described in Example 1. Synthesis of dimethylbenzophenone from an isomeric mixture of xylenes will produce a mixture of six dimethylbenzo-phenone isomers. Synthesis from pure p-xylene will produce only 2,5-dimethylbenzophenone; pure m-xylene will produce 2,4-, 2,5-, and 2,6-dimethylbenzophenone; and pure o-xylene will produce 2,3- and 3,4-dimethylbenzophenone. Specific isomeric mixtures are produced by a provident choice of the composition of the initial xylene mixture.

It should be understood that the foregoing disclosure emphasizes certain specific embodiments of the invention and that all modifications or alternatives equivalent thereto are within the spirit and scope of the invention as set forth in the appended claims.

We claim:

1. A method for preparing an aryl ketone comprising the following steps:
   (a) heating in a reaction vessel a reaction mixture comprising an aromatic hydrocarbon selected from the group consisting of benzene and methyl- and dimethyl-substituted derivatives of benzen-, an aromatic acyl halide selected from the group consisting of benzoyl chloride and methyl- and dimethyl-substituted derivatives of benzoyl chloride and a catalytic amount of iron (III) chloride to a temperature and for a time sufficient to substantially convert the aromatic acyl halide to aryl ketone and hydrochloric acid gas, under a pressure greater than atmospheric and sufficient to maintain the aromatic hydrocarbon substantially in a liquid form, the pressure being from about 100 pounds per square inch to about 450 pounds per square inch; and
   (b) venting the reaction vessel to permit the release of an amount of the hydrochloric acid gas sufficient to maintain the pressure in the reaction vessel between about 100 pounds per square inch to about 450 pounds per square inch.

2. The method of claim 1 wherein the aromatic hydrocarbon is present in a mole ratio of about 1:1 to about 5:1 of the amount of the aromatic acyl halide present in the reaction mixture.

3. The method of claim 1 wherein the catalytic amount of iron (III) chloride provided in the reaction mixture is from about 0.25% to about 3.0% of the amount of the aromatic acyl halide provided.

4. The method of claim 1 wherein the reaction mixture is heated to a temperature from about 150° C. to about 300° C.

5. The method of claim 1 wherein the reaction mixture is heated for a time of about 2 hours to about 15 hours.

6. The method of claim 1 wherein from about 70% to about 90% of the mole amount of the aromatic acyl halide provided in the reaction mixture is converted to aryl ketone.

7. A method for preparing an aryl ketone comprising the following steps in the following sequence:
   (a) heating in a reaction vessel a reaction mixture comprising an aromatic hydrocarbon selected from the group consisting of benzene and methyl- and dimethyl-substituted derivatives of benzene, aromatic acyl halide selected from the group consisting of benzoyl chloride and methyl- and dimethyl-substituted derivatives of benzoyl chloride and a catalytic amount of iron (III) chloride to a temperature and for a time sufficient to substantially convert the aromatic acyl halide to aryl ketone and hydrochloric acid gas, under a pressure greater than atmospheric and sufficient to maintain the aromatic hydrocarbon substantially in a liquid form, the pressure being from about 100 pounds per square inch to about 450 pounds per square inch;
   (b) venting the reaction vessel to permit the release of an amount of the hydrochloric acid gas sufficient to maintain the pressure in the reaction vessel between about 100 pounds per square inch to about 450 pounds per square inch;
   (c) distilling the reaction mixture to form a distillate comprising the aryl ketone product;
   (d) washing the distillate with a solution of sodium hydroxide;
   (e) washing the distillate with water;
   (f) redistilling the washed distillate to form substantially pure aryl ketone.

8. The method of claim 7 wherein the aromatic hydrocarbon is present in a mole ratio of about 1:1 to about 5:1 of the amount of the aromatic acyl halide present in the reaction mixture.

9. The method of claim 7 wherein the catalytic amount of iron (III) chloride provided in the reaction mixture is from about 0.25% to about 3.0% of the amount of the aromatic acyl halide provided.

10. The method of claim 7 wherein the reaction mixture is heated to a temperature from about 150° C. to about 300° C.

11. The method of claim 7 wherein the reaction mixture is heated for a time of about 2 hours to about 15 hours.

12. The method of claim 7 wherein from about 70% to about 90% of the mole amount of the aromatic acyl halide provided in the reaction mixture is converted to aryl ketone.

13. The method of claim 7 wherein the purified aryl ketone is from about 99.5% to about 99.9% pure.

14. A method for preparing an aryl ketone comprising the following steps:
   (a) heating a first reaction mixture comprising an aromatic hydrocarbon selected from the group consisting of benzene and methyl- and dimethyl-substituted derivatives of benzene and a catalytic amount of iron (III) chloride to a temperature and under a pressure greater than atmospheric and sufficient to maintain the aromatic hydrocarbon substantially in a liquid form, the pressure being from about 100 pounds per square inch to about 450 pounds per square inch;
   (b) mixing the first reaction mixture with a second reaction mixture comprising an aromatic acyl halide selected from the group consisting of benzoyl chloride and methyl- and dimethyl-substituted derivatives of benzoyl chloride to form a third reaction mixture;
   (c) incubating the third reaction mixture at a temperature and for a time sufficient to substantially convert the aromatic acyl halide to the aryl ketone and hydrochloric acid gas, under a pressure greater than atmospheric and sufficient to maintain substituted benzene substantially in a liquid form, the pressure being from about 100 pounds per square inch to about 450 pounds per square inch;

(d) venting the reaction vessel to permit the release of an amount of the hydrochloric acid gas sufficient to maintain the pressure in the reaction vessel between about 100 pounds per square inch to about 450 pounds per square inch.

15. The method of claim 14 wherein the aromatic hydrocarbon is present in a mole ratio of about 1:1 to about 5:1 of the amount of the aromatic acyl halide present in the reaction mixture.

16. The method of claim 14 wherein the catalytic amount of the iron (III) chloride provided in the reaction mixture is from about 0.25% to about 3.0% of the amount of the aromatic acyl halide provided.

17. The method of claim 14 wherein the first reaction mixture is heated to a temperature from about 150° C. to about 300° C.

18. The method of claim 14 wherein the third reaction mixture is heated to a temperature from about 150° C. to about 300° C.

19. The method of claim 14 wherein the third reaction mixture is incubated for a time of about 2 hours to about 15 hours.

20. The method of claim 14 wherein from about 70% to about 90% of the mole amount of the aromatic acyl halide provided in the reaction mixture is converted to aryl ketone.

21. A method for preparing an aryl ketone comprising the following steps in the following sequence:

(a) heating a first reaction mixture comprising an aromatic hydrocarbon selected from the group consisting of benzene and methvl- and dimethyl-substituted derivitives of benzene and a catalytic amount of iron (III) chloride to a temperature and under a pressure greater than atmospheric and sufficient to maintain the aromatic hydrocarbon substantially in a liquid form, the pressure being from about 100 pounds per square inch to about 450 pounds per square inch;

(b) mixing the first reaction mixture with a second reaction mixture comprising an aromatic acyl halide selected from the group consisting of benzoyl chloride and methyl- and dimethyl-substituted derivatives of benzoyl chloride to form a third reaction mixture;

(c) incubating the third reaction mixture at a temperature and for a time sufficient to substantially convert the aromatic acyl halide to aryl ketone and hydrochloric acid gas, under a pressure greater than atmospheric and sufficient to maintain the aromatic hydrocarbon substantially in a liquid form, the pressure being from about 100 pounds per square inch to about 450 pounds per square inch;

(d) venting the reaction vessel to permit the release of an amount of the hydrochloric acid gas sufficient to maintain the pressure in the reaction vessel between about 100 pounds per square inch to about 450 pounds per square inch;

(e) distilling the third reaction mixture to form a distillate comprising the aryl ketone product;

(f) washing the distillate with a solution of sodium hydroxide;

(g) washing the distillate with water;

(h) redistilling the washed distillate to form substantially pure aryl ketone.

22. The method of claim 21 wherein the aromatic hydrocarbon is present in a mole ratio of about 1:1 to about 5:1 of aromatic acyl halide present in the reaction mixture.

23. The method of claim 21 wherein the catalytic amount of the iron (III) chloride provided in the reaction mixture is from about 0.25% to about 3.0% of the amount of the aromatic acyl halide provided.

24. The method of claim 21 wherein the first reaction mixture is heated to a temperature from about 150° C. to about 300° C.

25. The method of claim 21 wherein the third reaction mixture is heated to a temperature from about 150° C. to about 300° C.

26. The method of claim 21 wherein the third reaction mixture is incubated for a time of about 2 hours to about 15 hours.

27. The method of claim 21 wherein from about 70% to about 90% of the mole amount of the aromatic acyl halide provided in the third reaction mixture is converted to aryl ketone.

28. The method of claim 21 wherein the purified aryl ketone is from about 99.5% to about 99.9% pure.

* * * * *